United States Patent
Morgan

(10) Patent No.: US 6,325,628 B1
(45) Date of Patent: Dec. 4, 2001

(54) TEMPORARY IMPLANT COMPONENTS, SYSTEM AND METHOD

(75) Inventor: Vincent J Morgan, Boston, MA (US)

(73) Assignee: Diro, Inc., Boston, MA (US)

( * ) Notice: Subject to any disclaimer, the term of this patent is extended or adjusted under 35 U.S.C. 154(b) by 0 days.

(21) Appl. No.: 09/581,062
(22) PCT Filed: Dec. 8, 1998
(86) PCT No.: PCT/US98/26149
 § 371 Date: Jun. 7, 2000
 § 102(e) Date: Jun. 7, 2000
(87) PCT Pub. No.: WO99/29256
 PCT Pub. Date: Jun. 17, 1999

Related U.S. Application Data
(60) Provisional application No. 60/069,088, filed on Dec. 10, 1997.

(51) Int. Cl.[7] .................................................. A61C 11/00
(52) U.S. Cl. ............................................ 433/173; 433/174
(58) Field of Search ................................ 433/172, 173, 433/213, 214

(56) References Cited

U.S. PATENT DOCUMENTS

| | | | |
|---|---|---|---|
| 4,738,623 | * | 4/1988 | Driskell .............................. 433/173 |
| 4,906,191 | * | 3/1990 | Söderberg ........................... 433/173 |
| 5,078,606 | * | 1/1992 | Söderberg ........................... 433/173 |
| 5,556,280 | * | 9/1996 | Pelak .................................. 433/172 |

* cited by examiner

Primary Examiner—Ralph A. Lewis
(74) Attorney, Agent, or Firm—John A. Haug

(57) ABSTRACT

A temporary dental prosthesis (60) which can be placed before, after or simultaneously with the placement of permanent implant i securely and accurately fixed to mounting assemblies (58). Each mounting assembly (58) has a combination implant/abutment member (10) screwed into a bore formed in the cortical bone with a smooth convex basal portion (12) received in a complimentary shaped recess formed at the entrance of the bore. A coping (30) is received on the head (16) of the combined implant/abutment member (10) and retained there by a pin (50) having a threaded portion (56) received in a threaded bore (24). The copings (30) and pins (50) are received in oversized bores formed in a blank temporary prosthesis and resin is injected around the copings and pins to secure the copings to the prosthesis at locations corresponding to the positions of the combined implant/abutment members (10).

17 Claims, 5 Drawing Sheets

TEMPORARY IMPLANT COMPONENTS, SYSTEM AND METHOD

This appln is a 371 of PCT/US98/26149 filed Dec. 8, 1998, which claims benefit of Provi. No. 60/069,088 filed Dec. 10, 1997.

FIELD OF THE INVENTION

This invention relates generally to dental implants and more particularly to a temporary prosthesis and method for using.

BACKGROUND OF THE INVENTION

The natural teeth of an individual may be lost as a result of dental disease or trauma, making it desirable to replace such teeth with one or more prosthetic devices. An example of a prosthetic device is a dental implant which is surgically positioned within the mandibular of maxillary alveolar bone.

One type of dental implant has a first implant member for placement in an osteotomy site in the alveolar bone of a patient. Following healing, a head member, commonly called an abutment, is mounted in or on the first implant member and a tooth simulating prosthesis or crown is then mounted on the abutment, or in the case of edentulous individuals, a bridge supporting abutment is mounted in the first implant member. A successful system of this type is disclosed in U.S. Pat. No. 4,738,623. In that patent, a first implant or root member having a first or outer end formed with a female socket circumscribed by a shoulder and having a suitable anchoring means, such as outwardly extending fins, is placed in an osteotomy site or implant receiving cavity in the alveolar bone with suitable surgical instruments and techniques. The first implant member is inserted into the cavity with the upper portion of the member a selected distance below the opening of the cavity, that is, below the crest of the bone, e.g., two or three millimeters. A healing plug is inserted into a female socket of the first implant member and particles of a natural and/or synthetic bone growth stimulating grafting material are then packed within the cavity around the shoulder of the implant member and the wound is then allowed to heal for four to six weeks or longer until osseointegration has been completed.

Following healing, the dentist surgically accesses and removes the plug and replaces it with an abutment. The abutment has a male portion received within the female socket and an intermediate, outer, generally hemispherical surface portion which may extend through the surface of the crest of the bone which had previously been reamed to form a complimentary configuration when forming the cavity. The hemispherical surface portion is non-irritating to soft tissue and promotes mucosal healing. A prosthetic device can be attached to the abutment.

During the healing process care must be taken to avoid the transmission of forces on the implant which could cause dehiscence of the integrating implant. In the case of an edentulous individual, this would mean that solid foods would have to be eschewed for the healing period of four to six weeks or longer.

SUMMARY OF THE INVENTION

It is an object of the invention to provide a temporary prosthesis, mounting components and a method for installing the prosthesis which can be used during the healing time of surgically positioned implants or whenever it is advantageous to attach a device to a temporary fixed implant. Another object of the invention is the provision of an apparatus and a method for securing a surgical stent or other device for use in implant surgery or for other purposes. Yet another object of the invention is the provision of an apparatus and a method by which a failing prosthesis can be secured on a temporary basis, that is, for a limited period of time.

Briefly stated, in accordance with the invention, single stage, combination implant/abutment members are screwed into the cortical bone between existing or planned permanent implants. The implant/abutment members have a head portion positioned above the mucosa. A precisely formed plastic coping is placed on each head portion and then a direct pick-up by and attachment of the coping to a temporary prosthesis can be effected or alternatively, a transfer pick-up impression of the copings can be done. With the use of implant analogs, a stone model can be poured for fabrication of the prosthesis extraorally. The prosthesis, for example a full or partial arch prosthesis, is then supported on the implant/abutment members spaced above the permanent implant sites thereby preventing transmission of transmucosal forces from the temporary prosthesis to the integrating implants caused by movement of the temporary prosthesis or food bolus. As a result, the patient is able to eat a more solid and diversified diet immediately post operatively. By means of the invention a temporary prosthesis can be securely and accurately placed, if desired, on the same day as that of the permanent implant surgery.

According to the preferred embodiment of the invention, the combination implant/abutment member is formed of biocompatible material, such as titanium or titanium alloy, with a hemispherically shaped basal portion adapted to be received in a complimentary formed seat in the cortical bone, a threaded post extending in one direction from the basal portion and a cylindrical head extending in an opposite direction from the basal portion. The cylindrical head is formed with at least one flat, and preferably a plurality of spaced apart flats, to facilitate rotary attachment of the members in the bores in the cortical bone. A tapered section is formed on the coronal portion of each head which serves as a coping seat and an axially extending bore is formed through the end face of the head portion with the outer portion of the bore being threaded and the inner portion of the bore being formed with a non-circular surface, e.g., hexagonal. The coping, formed of ceramic, metal or suitable moldable plastic, such as polycarbonate or acrylic, bondable to a prosthesis member, to be discussed, has an outer periphery generally frusto-conical in configuration with a first tapered bore extending from the larger end face and a second bore having a straight section of a selected length extending from the smaller end face and with a second tapered section formed at the end of the straight bore section extending to a junction with the first tapered bore. The first tapered bore is complimentary in angle and diameter to that of the coping seat on the head of the implant/abutment member for reception thereon. The second bore receives an elongated pin formed of biocompatible material such as the same material as that of the implant/abutment member having at one end a tapered portion complimentary in angle and diameter to that of the second taper of the coping which serves as a pin receiving seat and a threaded distal end for threaded reception in the threaded bore of the implant/abutment members. The main shaft portion of the pin has a diameter selected to closely fit in the straight bore of the coping and the other distal end is formed with a screw driving slot in the end face thereof. The length of the elongated pin is selected preferably to extend beyond the coping and at least partially through the temporary prosthesis.

BRIEF DESCRIPTION OF THE DRAWINGS

Other objects, advantages and details of the novel and improved temporary dental implant system and method of this invention appear in the following detailed description referring to the drawings in which.

DETAILED DESCRIPTION OF THE PREFERRED EMBODIMENT

Figure 1:
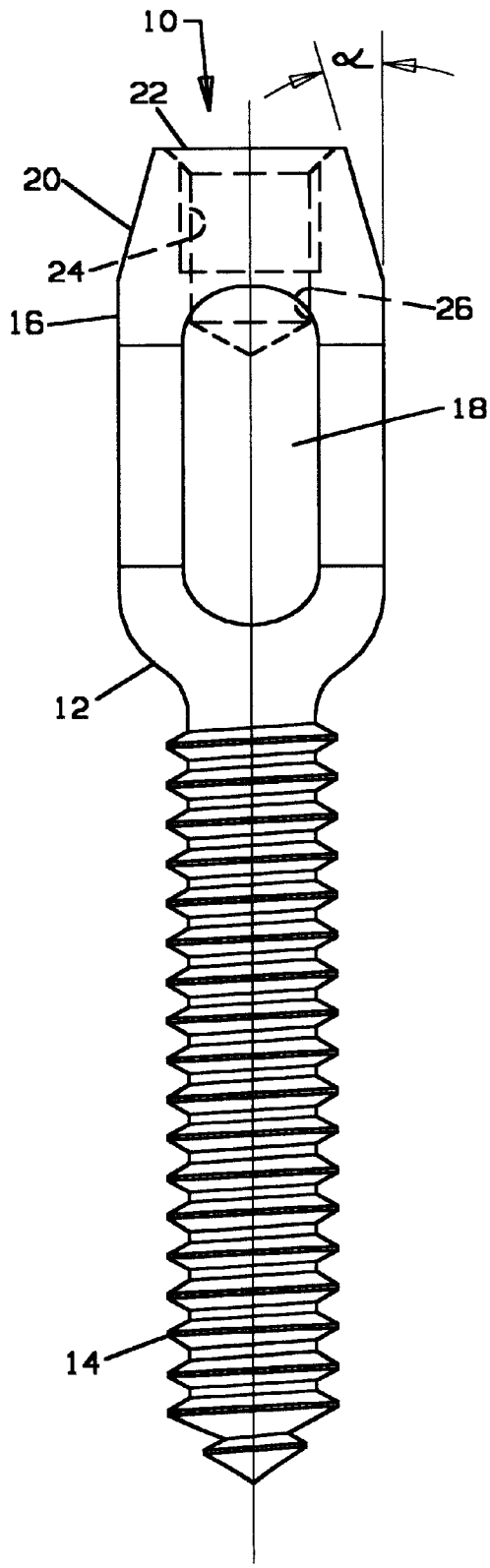
FIG. 1 is a front elevational view of a combination implant/abutment member of a mounting assembly made in accordance with the invention.
Figure 2:
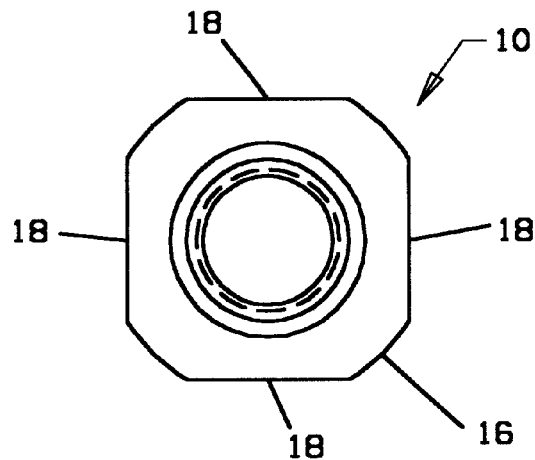
FIG. 2 is a top plan view of the FIG. 1 member.
Figure 3:
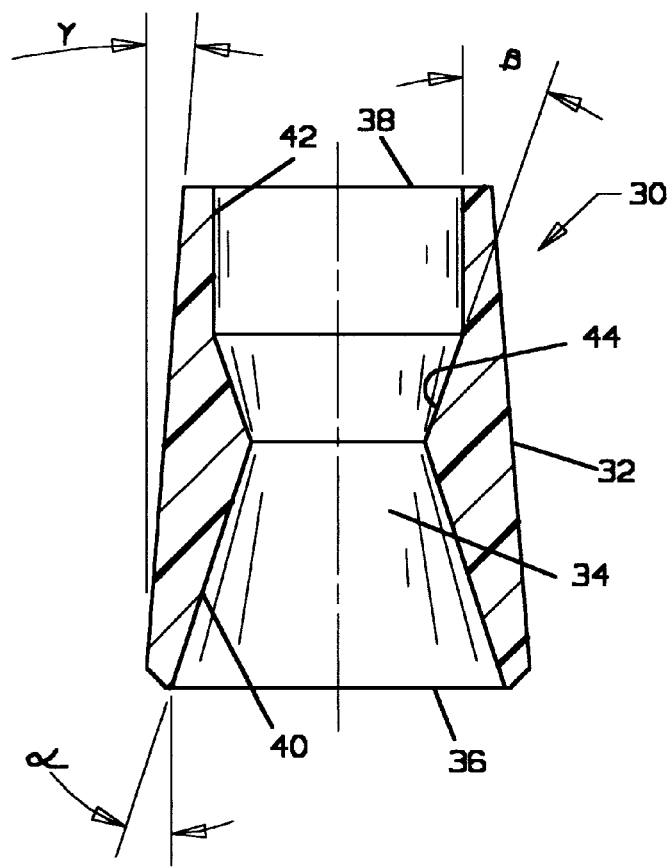
FIG. 3 is a cross sectional view of a coping receivable on the FIG. 1 member.
Figure 4:
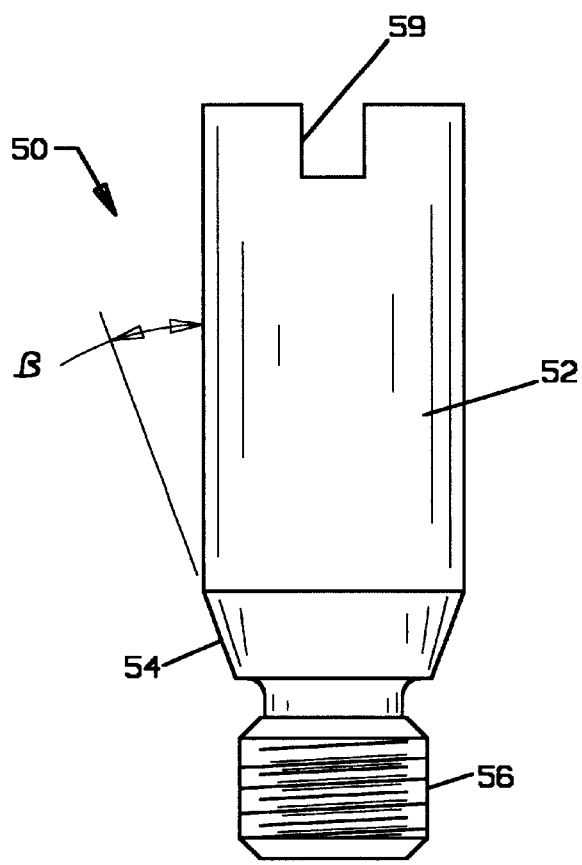
FIG. 4 is a front elevational view of a pin receivable in the FIG. 3 coping and attachable to the FIG. 1 member.

With reference to FIGS. 1 and 2, a combination implant/abutment member 10 comprises a smoothly curved convex basal portion 12, preferably hemispherical, with a post 14 of a selected length, e.g., 0.276, 0.394 or 0.550 inches, extending from the basal portion in one longitudinal axial direction and formed with cortical bone threads and a cylindrical head portion 16 extending from basal portion 12 in an opposite axial direction. Head 16 is formed with four spaced flats 18 to facilitate driving of the member into a bore formed in the cortical bone to be described below. It will be understood that the number of flats provided is a matter of choice. A tapered coping receiving seating surface 20 having a selected angle alpha, e.g., 18 degrees, is formed at the coronal portion of member 10 and a bore is formed through end 22 extending along the longitudinal axis of member 10. The outer portion 24 of the bore is threaded and the inner portion 26 is formed with a non-circular, i.e., hexagonal, portion to facilitate fastening in a bore by means of a latched dental hand piece screwdriver. Coping 30, shown in FIG. 3, is formed of suitable moldable plastic material, such as polycarbonate or acrylic to which the temporary prosthesis will bond, and preferably has a frusto-conical outer surface 32 formed with a selected angle gamma, e.g., 4 degrees, and a bore 34 extending between the larger end face 36 and the smaller face 38. A first tapered portion 40 extends from face 36 and has a taper angle alpha forming a surface having an angle and diameter complimentary to that of seating surface 20 of implant/abutment member 10. A straight section 42 of bore 34 extends from face 38 to a second tapered surface 44 which extends to a junction with the first tapered surface 40. Second tapered surface 44 is formed with a selected taper angle beta, e.g., 20 degrees, and serves as a pin receiving seat for pin 50, shown in FIG. 4. Pin 50 has an elongated cylindrical shaft 52 formed with a tapered seating surface 54 adjacent one end having a taper angle beta and a diameter selected so that surface 54 is complimentary in angle and diameter to seating surface 44 of coping 30. A threaded distal end portion 56 is receivable in threaded bore section 24 of implant/abutment member 10 to be discussed below. The opposite end of pin 52 is formed with a suitable screw slot 59 or other driving mechanism.

Figure 5:
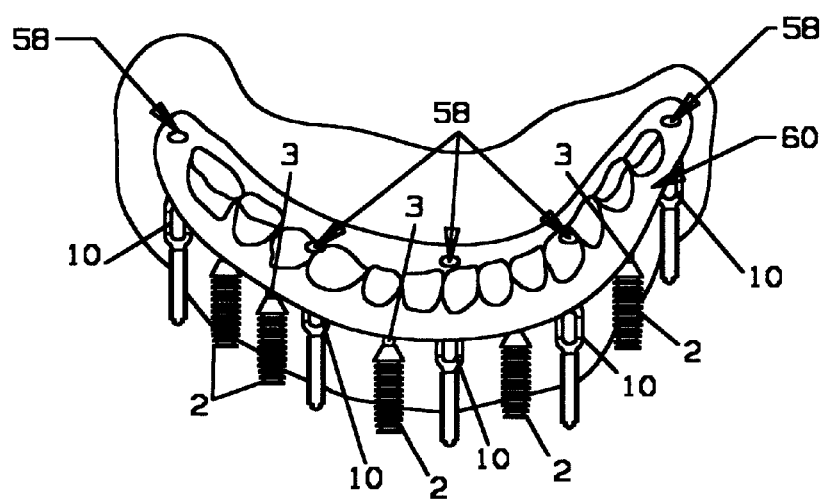
FIG. 5 is a perspective view of a broken away portion of a lower jaw showing a temporary full arch prosthesis mounted on combination implant/abutment members and spaced above permanent implant sites.
Figure 6:
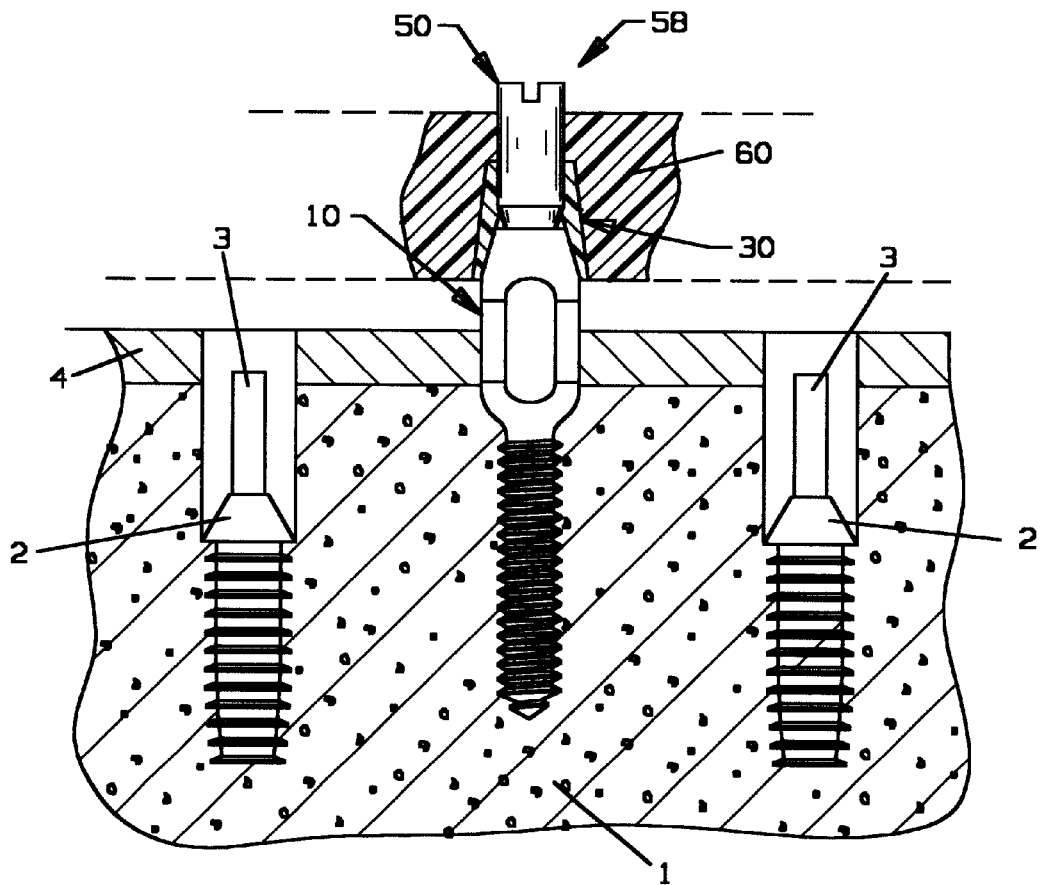
FIG. 6 is a cross sectional elevational view of a portion of a temporary prosthesis showing a mounting assembly implanted in a portion of a cortical bone which also shows permanent implant sites.

With reference to FIGS. 5 and 6, a schematic broken away portion of a lower jaw is shown with a plurality of combined implant/abutment members 10 implanted in cortical bone 1 along with proximately mounted permanent implants 2 having healing plugs 3 extending from abutment receiving sockets in the implants. The particular number, placement and type of implants 2 are a matter of choice. The time of placement of the permanent implants can be contemporaneous with the placement of implant/abutment members 10, before or after, if desired. Implant members 2, of any conventional type, are placed in the cortical bone using conventional implant surgical procedures, such as those discussed in U.S. Pat. No. 4,738,623, referenced above, the subject matter of which is incorporated herein by this reference. The location and number of implant/abutment members 10 are selected to provide solid, stable support for a prosthesis for a limited time period.

Figure 7:
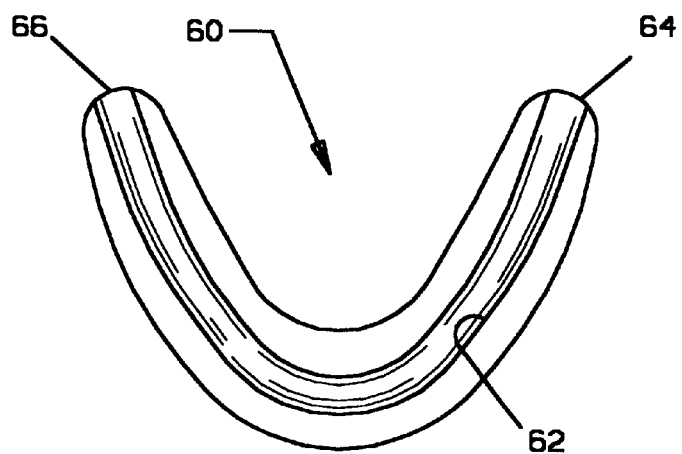
FIGS. 7 and 8 are bottom and top plan views, respectfully, of a temporary prosthesis blank.
Figure 8:
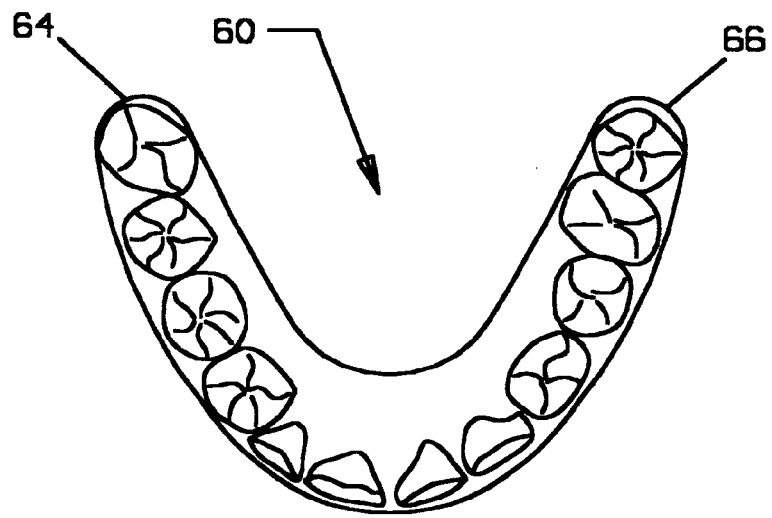
Figure 9:
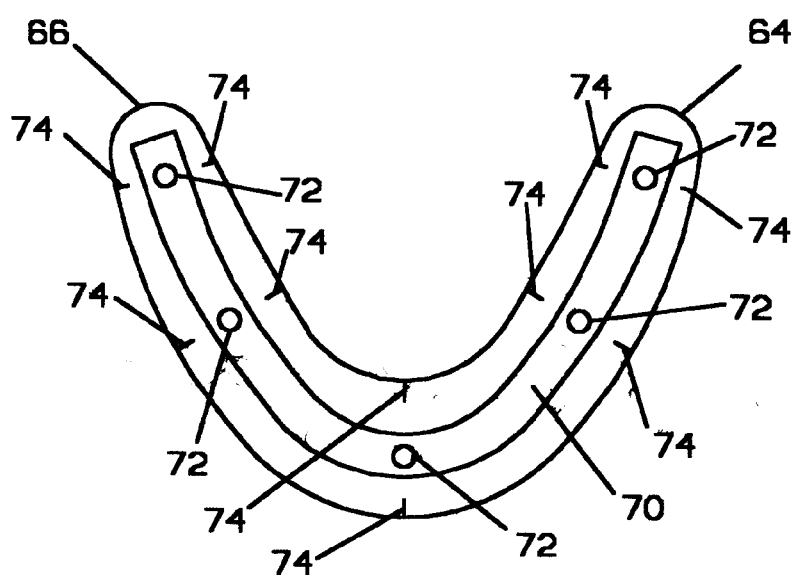
FIG. 9 is a bottom plan view, similar to FIG. 7, with transfer tape material placed in a tape receiving groove used to determine the location of the mounting assemblies fixed in the cortical bone.

Implant/abutment members 10 are implanted by first forming bores into the cortical bone at the selected locations with a conventional surgical bur. Preferably, a generally hemispherical recessed seat is formed at the entrance to the bore with a larger diameter bur and then a single stage, implant/abutment member 10 is screwed into the bone utilizing flats 18 with either manual or power tools. A pin 50 is then mounted in each member 10 with threaded portion 56 received in threaded bore portion 24. With reference to FIGS. 7–9, an elongated cord of flexible, relatively soft, impression material 70 is placed in a groove 62 extending between ends 64,66 of a suitable blank temporary prosthesis 60 on its bottom side and alignable with the cortical bone. Blank prosthesis 60 is formed of suitable plastic material, such as polycarbonate or acrylic. The blank temporary prosthesis 60 is then placed on members 10 with pins 50 attached thereto in the desired location relative to the cortical bone and pressed toward the mounting assemblies to make depressions 72 caused by pins 50. The prosthesis blank is removed and marked at 74. Cord 70 can then be removed and oversized bores formed through the prosthesis blank in alignment with the location of the previously disposed depressions 72.

Pins 50 are then removed from members 10 and a coping 30 is then placed on each implant/abutment member 10 with tapered surfaces 40 received on tapered seating surfaces 20. A pin 50 is then inserted in each respective coping and attached to member 10 by means of threaded portion 56 received in threaded bore portion 24 and with tapered surface 54 received on tapered surface 44 of coping 30. Prosthesis 60 is then placed on mounting assemblies 58 with pins 50 and copings 30 received in respective oversized bores. Epoxy, or similar material, is injected in the oversized bores around the pins and copings filling in the bores. As the epoxy sets, excess material is trimmed away leaving the prosthesis securely fastened to mounting assemblies 58, as shown in FIG. 6, spaced from the sites of permanent implants 2 so that no transmucosal force will be transmitted from the temporary prosthesis to or occlusal forces through the integrating permanent abutments 2 during the healing process. When the healing process is completed the pins can be unscrewed so that the temporary prosthesis, along with copings 30 can be removed. Implant/abutment members 10 can then be unscrewed and discarded and a permanent prosthesis can be installed supported on abutments placed in the now fully integrated permanent implants 2 in a known manner.

Pins 50 facilitate the removal and accurate placement of the prosthesis and the use of prefabricated copings 30 assure quality adaptation and minimize the clinician's chair time.

Although it is preferred to use pins 50, the design of the implant/abutment member 10, including the tapered mating surfaces 40 of the coping and 20 of the implant/abutment member, affords sufficient retention even if a pin is not used since sufficient resistance is provided by means of the internal walls of the threaded bore 24 and the tapered surfaces.

If desired, the temporary prosthesis can be formed by injecting or filling a shell or vacuum formed acrylic outline of the intended prosthesis with a suitable moldable material, such as acrylic, onto and around the seated copings of the combined implant/abutments.

It will be understood that a device also can be installed onto the combined implant/abutment(s) which may be used for non-prosthetic purposes, such as a support for anchorage in orthodontic or distraction osseogenesis purposes.

The invention minimizes dehiscence of integrating permanent implants caused by movement of a temporary prosthesis or food bolus while allowing a patient to eat a more solid and diversified diet immediately after placement of the temporary prosthesis on mounting assemblies 58. The invention allows for chair side or laboratory fabrication of the temporary prosthesis before or subsequent to permanent implant placement or independent of other implant placements.

In addition to allowing secure and accurate placement of a temporary prosthesis on the same day as permanent implants, the invention also allows salvaging of failing dental prosthesis on an interim basis. Another use of the invention is for the secure and accurate placement of surgical stents (templates) used in association with the placement of the permanent implants. Yet another use is as a means to secure other devices to bone, for example, one could secure an appliance which in turn could be used to secure other devices for a variety of purposes, such as aesthetics or for orthodontic purposes.

In view of the above, it will be seen that the various objects of the invention have been met. Various additional changes and modifications of the above described invention will be readily apparent to those skilled in the art and it is the intention that any such change or modification be deemed to come within the scope of the present invention as set forth in the appended claims.

What is claimed:

1. A temporary medical device comprising a support member having a plurality of bores formed therethrough, a combined implant/abutment member having a post formed with bone screw threads receivable into a bore formed in a bone, the member having a head portion formed with a coping receiving seating surface and a coping having a bore extending therethrough removably received on the coping receiving seating surface and extending into a respective bore of the support member and fixedly attached to the support member, the head portion extending above the bone a selected distance to space the support member from the bone.

2. A temporary medical device according to claim 1 in which the head of the combined implant/abutment member has a top end face and a threaded bore is formed through the top end face and further comprising a retention pin having a threaded portion, the pin received through the bore of the coping and threadingly attached to the threaded bore in the implant/abutment member.

3. A temporary medical device according to claim 2 in which the retention pin is formed with a screw driver slot in an end face thereof.

4. A temporary medical device according to claim 1 in which the bore in the coping has a tapered surface and the head portion has a tapered seating surface complimentary in configuration to that of the coping and the tapered surface of the coping is received on the seating surface of the head portion.

5. A temporary medical device according to claim 4 in which a second tapered surface is formed in the bore of the coping and the head portion is formed with an end face having a bore having a threaded portion extending through the end face into the head portion and further comprising a retention pin having a tapered surface and a threaded distal end, the pin received through the bore in the coping with the tapered surface of the pin received on the second tapered surface of the coping and the threaded distal end of the pin received in the threaded bore in the head portion.

6. A temporary medical device according to claim 5 in which the threaded bore has a second non-circular portion to facilitate driving of the implant/abutment member into a bore in a bone.

7. A temporary medical device according to claim 1 in which the head has an outer periphery formed with at least one vertically extending flat surface portion IQ facilitate driving of the implant/abutment member into a bore formed in a bone.

8. A temporary medical device according to claim 1 in which the coping is formed of plastic material.

9. A temporary medical device according to claim 1 in which the coping is formed of ceramic.

10. A temporary medical device according to claim 1 in which the coping is formed of metal.

11. A temporary medical device according to claim 1 in which the combined implant/prosthesis has a smooth, convex shaped basal portion from which the threaded post extends.

12. A temporary medical device according to claim 11 in which the convex shaped portion is generally hemispherical.

13. A mounting assembly for a temporary medical device comprising, a combined implant/abutment member having a head portion with a smooth, convex shaped basal portion, a threaded post formed with a bone screw thread extending from the basal portion, the head having a tapered, coping receiving surface and an end face with a bore formed through the end face into the head portion with at least a portion of the bore threaded, a coping having a bore extending from a first end face to an opposed, second end face, the bore formed with a first tapered surface complimentary in angle and diameter to the seating surface of the head, a second tapered surface formed in the bore of the coping forming a pin receiving seating surface, a pin having a threaded distal end and a tapered surface portion adjacent to the distal end, the tapered surface portion of the pin having an angle and diameter complimentary to the second tapered surface of the coping and the threaded distal end being threadingly receivable in the threaded bore of the head portion, the coping being receivable on the head portion with the pin received through the bore of the coping and threadingly attached to the head portion and retaining the coping on the head through the tapered surface of the pin and the second tapered surface of the coping.

14. A mounting assembly according to claim 13 in which the combined implant/abutment member is formed of titanium.

15. A method of installing a temporary dental prosthesis in the mouth of an individual comprising the following steps:
- forming a plurality of bores in the cortical bone, each with a hemispherical recess in the bone at the entrance to the respective bore,
- screwing into each respective bore a threaded post of a combined implant/abutment member having a post formed with bone screw threads with the bone threads engaging the cortical bone, the post extending from the hemispherically shaped basal portion of a head and screwing the post into the bone until the basal portion is seated in the recess,
- placing a blank temporary prosthesis over the combined implant/abutment members and marking the location of the combined implant/abutment members on the prosthesis,
- taking the prosthesis away from the combined implant/abutment members and forming bore through the prosthesis at each marked location of the combined implant/abutment members,
- placing a coping on the head of each combined implant/abutment member,
- placing the prosthesis over the combined implant/abutment members with the copings received in respective bores of the prosthesis, and
- injecting resin into each of the bores of the prosthesis around the copings to fix the prosthesis to the copings.

16. A method according to claim 15 further comprising the step of attaching the copings to the combined implant/abutment members by a threaded pin received through a bore formed in each respective coping.

17. A method of installing a temporary dental prosthesis in the mouth of an individual comprising the following steps:
- forming a plurality of bores in the cortical bone, each with a hemispherical recess in the bone at the entrance to the respective bore,
- screwing into each respective bore a threaded post of a combined implant/abutment member having a post formed with a bone screw thread extending from a hemispherically shaped basal portion of a head, the post being screwed into the respective bore until the basal portion is seated in the recess,
- attaching a coping to each combined implant/abutment member by a threaded pin received through a bore formed in each respective coping,
- forming a hollow shell of an intended prosthesis and placing the hollow shell of the intended prosthesis over the combined implant/abutment members and filling the hollow shell onto and around the copings of the combined implant/abutment members with a suitable molding material.

* * * * *